(12) United States Patent
Hvostoff et al.

(10) Patent No.: US 12,076,358 B2
(45) Date of Patent: Sep. 3, 2024

(54) COMPOSITION OF DESMODIUM AND TRIVALENT CHROMIUM, AND OCULAR USE

(71) Applicant: Laboratoires THEA, Clermont-Ferrand (FR)

(72) Inventors: Sophie Hvostoff, Mennecy (FR); Rima Yazbeck, Ramonville Saint Agne (FR)

(73) Assignee: LABORATOIRES THEA, Clermont-Ferrand (FR)

( * ) Notice: Subject to any disclaimer, the term of this patent is extended or adjusted under 35 U.S.C. 154(b) by 172 days.

(21) Appl. No.: 17/593,239

(22) PCT Filed: Mar. 23, 2020

(86) PCT No.: PCT/IB2020/052694
§ 371 (c)(1),
(2) Date: Sep. 13, 2021

(87) PCT Pub. No.: WO2020/194166
PCT Pub. Date: Oct. 1, 2020

(65) Prior Publication Data
US 2022/0152140 A1 May 19, 2022

(30) Foreign Application Priority Data
Mar. 25, 2019 (FR) ...................................... 1903045

(51) Int. Cl.
*A61K 36/48* (2006.01)
*A61K 33/24* (2019.01)
*A61K 45/06* (2006.01)
*A61P 27/02* (2006.01)

(52) U.S. Cl.
CPC ............. *A61K 36/48* (2013.01); *A61K 33/24* (2013.01); *A61K 45/06* (2013.01); *A61P 27/02* (2018.01)

(58) Field of Classification Search
CPC ......... A61P 27/02; A61K 36/48; A61K 33/24; A61K 45/06
See application file for complete search history.

(56) References Cited

U.S. PATENT DOCUMENTS

2001/0031744 A1* 10/2001 Kosbab ............... A61K 36/9068
514/474

FOREIGN PATENT DOCUMENTS

EP         3273947         9/2016
JP      2008520576    *   6/2008  ............... A61P 31/06

OTHER PUBLICATIONS

Adil Haimeur, et al, The Role of Odontella aurita, a Marine Diatom Rich in EPA, as a Dietary Supplement in Dyslipidemia, Platelet Function and Oxidative Stress in High-Fat Fed Rats, 11 Lipid Health Dis. 147 (Year: 2012).*
Qinghua Wu, et al, The Antioxidant, Immunomodulatory, and Anti-inflammatory Activities of Spirulina: An Overview, 90 Arch. Toxicol. 1817 (Year: 2016).*
JP 2008520576 Machine Translation (Year: 2008).*
Francois Muanda, et al, Chemical Composition and, Cellular Evaluation of the Antioxidant Activity of Desmodium adscendens Leaves, 2011 Evidence-Based Complementary and Alternative Medicine (Article ID 620862) (Year: 2011).*
Addy et al., "An extract of Desmodium adscendens inhibits NADPH-dependent oxygenation ofarachidonic acid by kidney cortical microsomes", Phytotherapy Research, vol. 6, Issue 5, p. 245-250.
Addy, "Several Chromatographically DistinctFractions of Desmodium adscendensInhibit Smooth Muscle Contractions", International Journal of Crude Drug Research, vol. 27, 1989, Issue 2, p. 81-91.
Areds Report No. 8, "A Randomized, Placebo-Controlled, Clinical Trial of High-Dose Supplementation With Vitamins C and E, Beta Carotene, and Zinc for Age-Related Macular Degeneration and Vision Loss", Arch Ophthalmol. Oct. 2001 ; 119(10): 1417-1436.
Areds Report No. 9, "A Randomized, Placebo-Controlled, Clinical Trial of High-DoseSupplementation With Vitamins C and E, Beta Carotene, and Zincfor Age-Related Macular Degeneration and Vision Loss", Arch Ophthalmol. Oct. 2001; 119(10): 1417-1436.
Cohen, "[Vitamins for prevention of age related maculardegeneration: efficacy and risk]", Bull Soc Belge Ophtalmol, 2006;(301):33-6.
Magielse et al., "Antihepatotoxic activity of a quantified Desmodiumadscendens decoction and D-pinitol againstchemically-induced liver damage in rats", J Ethnopharmacol, Mar. 7, 2013;146(1):250-6.
Mcmanus et al., "An activator of calcium-dependent potassiumchannels isolated from a medicinal herb", Biochemistry, Jun. 22, 1993;32(24):6128-33.
Rastogi et al. "An ethnomedicinal, phytochemical andpharmacological profile of Desmodium gangeticum(L.) DC. and Desmodium adscendens (Sw.) DC", J Ethnopharmacol, Jun. 22, 2011;136(2):283-96.
Rastogi et al., "An ethnomedicinal, phytochemical andpharmacological profile of Desmodium gangeticum(L.) DC. and Desmodium adscendens (Sw.) DcC", J Ethnopharmacol, Jun. 22, 2011;136(2):283-96.

(Continued)

*Primary Examiner* — Sean M Basquill
(74) *Attorney, Agent, or Firm* — Pearne & Gordon LLP

(57) ABSTRACT

The composition comprises a preparation of *Desmodium* and a trivalent chromium salt. The composition preferably comprises *Desmodium adscendens* or *Desmodium gangeticum* and chromium chloride, chromium nicotinate or chromium picolinate. It is formulated alone or with other active substances, excipients or additives, for oral administration as a medicinal product, phytomedicinal product, medical device, dietary supplement or admixture to a food product. It is intended for use in the prevention or treatment of a retinal degenerative disease such as age-related maculopathy (ARM) and dry or wet age-related macular degeneration (ARMD).

21 Claims, 2 Drawing Sheets

(56) References Cited

OTHER PUBLICATIONS

Vaghela et al., "Pharmacological Activities Of Desmodium Gangeticum: An Overview", Pharma Science Monitor, vol. 4, Issue—4, Jul.-Sep. 2013.
International Search Report issued in application No. PCT/IB2020/052694, dated Jun. 4, 2020.

* cited by examiner

COMPOSITION OF DESMODIUM AND TRIVALENT CHROMIUM, AND OCULAR USE

CROSS-REFERENCE TO RELATED APPLICATIONS

This application is the U.S. National Phase under 35 U.S.C. § 371 of International Application PCT/IB2020/052694, filed Mar. 23, 2020, which claims the benefit of French Application No. 1903045, filed Mar. 25, 2019, the disclosures of which are incorporated by reference herein in their entireties.

BACKGROUND

This invention relates to a composition comprising a preparation of *Desmodium* and a trivalent chromium salt and its use to treat eye conditions, particularly for preventing the formation and development of drusen precursors of AMD.

AMD (Age-Related Macular Degeneration) consists of a degradation of part of the retina (the macula) that can lead to loss of central vision. It is the leading cause of low vision in developed countries among people over the age of fifty. By 2040, early AMD is expected to affect 14.9 million to 21.5 million people in Europe, and between 3.9 million and 4.8 million for the advanced form (*Ophthalmology*, 2017, *Washington sl/ab/APMnews*).

The disease begins with a non-degenerative phase, called age-related maculopathy (ARM) or early dry phase. ARM may remain stable for a long period of time, but in half of the cases and under the influence of various factors, it evolves into one of the late degenerative forms: the atrophic form, called advanced dry AMD, or the wet form, called exudative AMD. Both lead to irreversible degradation of the macula and loss of central vision affecting one or both eyes. There is currently no treatment for dry and/or atrophic AMD. As for the wet form, the degeneration process may be slowed down by injections of monoclonal antibodies. However, this does not prevent the frequent evolution towards the incurable atrophic form for the moment.

In its early phase, ARM is characterized by the accumulation of small whitish deposits in and around the macula. These deposits, also called druses or drusen, are visible during a simple fundus examination. A normal process of ocular aging, they become more abundant with an inflammatory phenomenon leading to an accentuated destruction of the retina in patients with AMD.

Numerous studies have been and continue to be conducted to understand the mechanisms at work in retinal dysfunction and find ways to remedy them. One hypothesis considers that the retinal pigment epithelium cells deteriorate with aging, causing an insufficient supply of oxygen to the photoreceptor cells, which can no longer send visual signals to the brain. This causes less destruction of the waste that accumulates in the eye. This accumulation leads to the deposition of drusen, precursors of AMD. Another hypothesis is that the underlying blood vessels that supply nutrients and release waste from the retinal pigment epithelium and photoreceptors are not functioning well. The consequence is a lack of oxygen and an accumulation of waste. Hypoxia causes the release of a vascular growth factor, which in turn induces a compensatory mechanism through the formation of new abnormal blood vessels.

In 2002, a team of American researchers studied fundus druses of AMD-affected and non-diseased eyes. They found protein changes within the druses of sufferers, with alterations that may be due to the oxidation of lipids and sugars. A molecular link is thus established between oxidative alterations and AMD (Crabb J. W., *Proc Natl Acad Sci USA*, 2002, *Early Edition* 10.1073/pnas 222551899).

Many questions remain open concerning the onset and causes of the pathological evolution. Besides genetic theories evoking deficiencies in epithelial enzymes, explanations based on nutritional deficiencies, particularly in antioxidant vitamins, have been developed. In addition, separate studies of vitamin C, vitamin E, carotenoid, or zinc have yielded controversial results regarding the link to AMD and the value of supplementation.

The Age Related Eye Disease Study (AREDS) was the first randomized controlled trial to investigate the effect of antioxidant vitamins and zinc alone or together, at doses well above the recommended daily allowance (*Arch. Ophthamol.*, 2001; 119:1417-36). The study evaluated the protective effect of a combination of antioxidants at high doses of vitamin C (500 mg/d), Vitamin E (400 Ul/d), beta carotene (15 mg/d), and zinc (80 mg/d). This combination has been shown to be protective in patients with previous central vision loss in one eye (AREDS stage 4) and in patients with large drusen or geographic atrophy without central involvement (AREDS stage 3).

The results obtained after six years of follow-up thus make it possible to confirm the benefit of preventive therapy by food supplementation with antioxidant vitamins and zinc at the intermediate stage of AMD. However, no recommendation for such supplementation could be formally made for patients with early forms of ARM or moderate AMD, with drusen of less than 125 µm, corresponding to categories 1 and 2 of the AREDS classification.

In addition, the AREDS study draws attention to the risks of a toxic accumulation of vitamin A in the pigment epithelium. Its prescription in high doses is also suspected of aggravating the toxic accumulation of metabolic products that promote atrophy (Cohen S. Y., *Bull. Soc. beige Ophthalmol.*, 2006, 301, 33-36).

On the other hand, beta-carotene presents a risk in patients who smoke, which has led the pharmaceutical industry to propose other cocktails in which it is replaced by other pigments, mainly by lutein and zeaxanthin or meso-zeaxanthin. However, no randomized and controlled study can confirm the effectiveness of such cocktails (ibid.). Subsequently, other molecules were introduced into cocktails intended for food supplementation for the eye, such as omega-3 fatty acids, particularly DHA (docosahexaenoic acid). However, no dietary supplement currently available is completely satisfactory.

SUMMARY

Therefore, there is a need to develop effective compositions so as to offer an efficient treatment of maculopathies at an early stage to relieve patients affected by the development of drusen, making it possible to avoid a worsening of symptoms leading to degenerative forms of AMD and that do not present risks associated with their intake or adverse effects on certain groups of people.

It was surprisingly discovered that by combining *Desmodium* with a trivalent chromium salt, an effective action on drusen is achieved, leading to their regression, even to their disappearance.

Therefore, the subject-matter of this invention is a composition comprising a preparation of *Desmodium* and a trivalent chromium salt.

*Desmodium* is a herbaceous plant that is part of the Fabaceae, whose geographical area goes from the equatorial zone to the humid regions of the tropical zone of West Africa. About 300 species of the genus *Desmodium* exist in the world, and 25 different species are used in traditional medicines around the world. Those most widely used are listed in the Indian and Chinese pharmacopeia, such as *D. Girans, D. Latifolium, D. Polycarpum, D. Pullchellium, D. Tiliaffolium, D. Trifiorum, D. Styracifolium, D. Incanum, D. Canadense, D. Sessilifolium, D. Illinoensis*. To these, we must add *Desmodium adscendens*, and *Desmodium gangeticum*, whose numerous pharmacological activities have been described, including hepatoprotective, immunomodulatory, antiasthmatic, muscle relaxant, anti-ulcer, anti-inflammatory, cardio-protective properties (Rastogi S. et al., *Journal of Ethnopharmacology*, 2011, 136-2: 283-296) In 2013, a laboratory in Madagascar obtained approval from the Ministry of Health for the production of *Desmodium adscendens* and markets it as a phyto-drug which has received marketing authorization (AMM).

Few components have been isolated from *Desmodium adscendens*. The components that were first identified in its leaves in an aqueous medium are triterpenoid saponins, tetrahydro-isoquinolines, tryptamine derivatives (phenylethylamine and indole-3-alkylamines) (Addy M. E., *Internal Journal of Crude Drugb Research* 1989; 27:81-91). Subsequently, among the saponins, three components that have been extensively studied in pharmacology for their agonistic action on certain calcium channels were isolated: dehydrosoyasaponin I (DHS1), the majority compound, and soyasaponins I and III (Mc Manus O. B. et al., *Biochemistry*, 1993; 32:6128-33). Tyramine and hordenine have also been isolated (Addy M E et al., *Phytotherapy Research*, 1992; 6:245-50). More recently, a sugar has been identified in the leaves and stems, d-pinitol (Malgielse J. et al., *Journal of Ethnopharmacology*, 2013; 146: 250-56). Work on flavonoids has identified the presence of vitexin and isovitexin (flavone heterosides) (Heard O., 1994, *Thèse d'état pour le doctorat en pharmacie, faculté de Tours*).

*Desmodium adscendens* is the most often cited, but *Desmodium gangeticum* could be substituted. In one embodiment of the composition according to the invention, the preparation of *Desmodium* is a *Desmodium adscendens*, or *Desmodium gangeticum* powder obtained by grinding the leaves, stems or aerial parts of the plant. This powder is easy to store and may be subsequently introduced into formulations comprising other active ingredients and excipients in dry, paste, or liquid phase dosage forms.

Trivalent chromium (Cr III), atomic mass 52, is necessary for the utilization of fatty acids and proteins, as well as carbohydrates. It is an insulin potentiator, and as an insulin cofactor, it is also involved in lipid metabolism. Deficiency may lead to heart problems, metabolic disturbances, and diabetes, while excessive absorption may lead to problems such as rashes. In humans, the recommended nutritional intake (ANC) is 40 µg/d according to Directive 2008/100/CE. Chromium III may be provided in the form of a salt, in combination with a counterion such as a chloride, nicotinate, or picolinate. It is also available as an enriched brewer's yeast.

According to one embodiment of the composition according to the invention, the chromium salt is selected from chromium chloride, chromium nicotinate and chromium picolinate. Chromium picolinate and chromium nicotinate (or chromium (III) picolinate and chromium (III) nicotinate, respectively according to the IUPAC nomenclature), are isomeric compounds of the formula $Cr(C_6H_4NO_2)_3$ having an average molar mass of 418.33 g. Chromium chloride is advantageously used in the form of a solution, available in a dose ampoule, for example.

According to one embodiment of the invention, the composition comprises from 0.2 mg to 1.2 mg of chromium III per gram of *Desmodium*. Preferably, it comprises 0.25 mg to 0.5 mg of chromium III per gram of *Desmodium* and more preferably 0.33 mg per gram of *Desmodium*.

The composition according to the invention may be pure, i.e., containing only its essential components, namely *Desmodium* and chromium salt, but may also include other compounds having a complementary action with the essential components. Thus, the composition may comprise from 30% to 100% of the *Desmodium* and chromium salt preparation, by mass, relative to the total mass of the composition. Among the ingredients likely to accompany the *Desmodium*-Cr III combination, we find vitamins, and in particular vitamins with an antioxidant effect, such as ascorbic acid (C), vitamin E, riboflavin (B2), niacin (B3), pyridoxine (B6), folic acid (B9), or cobalamin (B12). Other vitamins may also be incorporated into the composition, such as choline (B4), thiamine (B1), biotin (B8). Thus, in one embodiment, the composition according to the invention comprises at least one vitamin selected from vitamin C, vitamin E, vitamin B1, vitamin B2, vitamin B3, vitamin B4, vitamin B6, vitamin B8, vitamin B9 and vitamin B12.

According to another embodiment of the invention, the composition may comprise at least one pigment selected from lutein and zeaxanthin. These yellow-orange pigments belong to the family of light-filtering carotenoids in plants (although they have no provitamin A activity), and are present in very high concentrations in the retina. They have antioxidant properties and are proposed for their role in protecting fragile tissues against the aggression of sunlight.

The composition which is the subject-matter of the invention, may also include ingredients rich in fatty acids of the omega-3 type, and in particular in DHA (docosahexaenoic acid), in EPA (eicosapentaenoic acid), and/or in ALA (alpha-linolenic acid). DHA is involved in virtually all organs. It is the most abundant omega-3 in the brain and the retina. A study that warned about the effects of omega-3 from fish oils used in dietary supplements for ocular purposes (prostate cancer in men (BRASKY et al., 2013, *Journal of the National Cancer Institute*), gave preference to plant sources, in particular microalgae such as *Schizochytrium* or *Odontella aurita*, containing omega-3 in large quantities. These microalgae have the advantage of also being rich in xanthophyll pigments (especially lutein). From a nutritional point of view, *Odontella aurita* presents a profile of particularly interesting compounds, especially since it is the first marine microalgae to have been authorized for human nutrition. It produces long-chain polyunsaturated fatty acids, mainly EPA and DHA, molecules essential for the development of the central nervous system, vision, and protection of the cardiovascular system (EFSA, 2011). Moreover, in *Odontella aurita*, the omega-3/omega-6 ratio is about 8, which helps to compensate for the imbalance of industrial foods that are too rich in omega-6 (omega-3/omega-6 ratio of 0.03 to 0.10). It is marketed in the form of powder or oil. *Schizochytrium*, also of marine origin, contains high amounts of DHA. It is cultivated for the production of DHA, its oil being intended in particular for human consumption in food supplements and additives. The most frequently cited microalgae capable of producing significant amounts of DHA are those belonging to the genera *Schizochytrium, Odontella, Crypthecodinium, Phaeodactylum*, and *Ulkenia*. Many other plants are also popular sources of Omega-3. For example, flaxseed, walnut oil, rapeseed oil, dry walnuts, watercress, cabbage, spinach, etc., which are known to the skilled person for this type of application, may be used. These components can be provided in the form of a dry microalgae grind, or after extraction, in the form of an oil or a fatty paste.

In an alternative embodiment, the composition according to this invention comprises a source of fatty acids of omega-3 type. Preferably, the omega-3 source is selected from a *Schizochytrium* preparation, an *Odontella aurita* preparation, a flax seed preparation, or a mixture thereof.

According to one embodiment, the composition according to the invention comprises from 30% to 75% *Desmodium* and chromium salt, from 10% to 30% vitamins, and from 0.5% to 2.5% lutein and zeaxanthin, and from 25% to 60% of a *Schizochytrium* or *Odontella* oil preparation, by weight, with respect to the total weight of the composition.

According to a preferred embodiment, the composition according to the invention comprises from 60% to 65% *Desmodium* and chromium salt, from 15% to 18% vitamins, from 0.75% to 1.5% lutein and zeaxanthin, and from 30% to 40% of a *Schizochytrium* or *Odontella* oil preparation, by weight relative to the total weight of the composition.

According to one interesting characteristic, the composition according to the invention further comprises a dry preparation of *Aphanizomenon flos-aquae* (or more simply AFA) or *Spirulina*. AFA is a blue green alga, also known as Super Blue Green Algae, native to the Klamath Lake in the western United States. Its composition is rich in micronutrients, including the phycocyanin blue pigment, and in omega-3 polyunsaturated fatty acids, making it a frequently used supplement in food supplements. It is generally prepared by gentle drying, protecting its components, and then reduced to a powder. *Spirulina* is also appreciated for its high micronutrient content.

Optionally, the composition which is the subject-matter of the invention may contain zinc. Zinc is present at a high concentration in the retina, and plays a very important role in the antioxidant defense mechanisms. According to the previously mentioned AREDS study, no effect in patients with drusen less than 125 µm was found, but a protective effect in AMD stages 3 and 4 was noted for zinc combined with vitamins, helping to reduce macular damage better.

Most of the composition components that are the subject-matter of the invention may be in a solid state, generally in the form of fine powders that are easy to prepare, stabilize for preservation, and store. Therefore, one may easily choose a particular formulation and proceed to a mixture that will itself be in a solid state and easily preserved. Depending on the formulation selected, the composition may be "pure," i.e., it contains only the active ingredients selected. However, some components are not pure themselves but obtained and marketed in a carrier phase. During the manufacture of the composition, these carriers will therefore be found in the mixture. It is also possible that an excipient or additive might be introduced into this mixture, such as a binding agent (e.g., microcrystalline cellulose), an anti-caking agent (e.g., magnesium stearate), a coloring agent, or other acceptable pharmaceutical excipients well known to those skilled in the art, as suitable for use in this type of composition. In this description, it should be understood that unless otherwise indicated, the compounds mentioned are active ingredients without taking into account the possible additives and excipient or the dilution in a carrier phase.

In any event, all the additives and excipients used in the composition are suitable for food or oral pharmaceutical use and are selected from products of plant origin as far as possible. The powdered mixture may then be administered as is, with the patient taking a dose with a measuring spoon or other means at their disposal. The mixture may also be put in a pre-dosed unit dosage form, such as tablets, capsules, softgels, or others. The capsule dosage form preferably uses a shell of vegetable origin, for example, hydroxypropyl methyl cellulose (HPMC), of 70 mg to 75 mg.

Thus, according to one embodiment, the composition is formulated alone or with at least one excipient or additive, to be administered orally in the form of capsules, tablets, softgels, or alternatively in liquid form, in dose ampoules or a bottle. It is specified that all the ingredients constituting the composition are not necessarily formulated in a single dose-pack but may be divided into two (or more) dose-packs to be taken concomitantly or spread over the day. For example, part of the components may be contained in a capsule, and the remaining components in a second capsule, or a tablet, or in liquid state, in a bottle, or an ampoule. The principle is that the different components are administered at short intervals from each other so that they act simultaneously.

According to an advantageous embodiment, the composition, which is the subject-matter of the invention, the composition is administered daily, in the form of one or two dose-packs. Thus, for example, it may be administered so as to provide a daily dose of 0.2 g to 1.0 g of *Desmodium* and chromium III, it being understood that the *Desmodium* and chromium III are in the relative proportions defined above. Preferably, one can provide a daily dose of 0.5 g to 0.7 g of *Desmodium* and 0.19 mg to 0.21 mg of chromium III. The daily dose may be administered in one dose, or divided into two or three doses distributed throughout the day.

The above-described composition can be prescribed as a medication for the therapeutic treatment of visual disorders related to the appearance of drusen on the retina. Such medication may also be administered as a preventive measure in order to anticipate phenomena that could aggravate health problems or lead to their appearance. More particularly, it may be considered as a phyto-medication since phyto-medications are medications in which the active ingredient comes from an entire plant or a part of this plant. According to certain regulations, it may be considered a medical device. Also, the composition may be considered as a food supplement for ocular purposes and recommended as such. In some cases, it will be interesting to include it in a food product so that the intake is without effort while respecting dietary recommendations for the prevention of AMD.

Thus, the composition which is the subject-matter of this invention may be used as a medicament, phyto-medication, medical device, food supplement, or mixed with a food product.

It is thus intended to be used to prevent or treat a degenerative pathology of the retina selected from age-related maculopathy (AMM), dry age-related macular degeneration (AMD), and exudative age-related macular degeneration. In particular, it may be prescribed to prevent the appearance of drusen, and if necessary, to obtain the reduction or elimination of drusen. In the treatment of AMD, both early dry and advanced dry forms are targeted, as well as wet (or exudative) AMD.

It may be prescribed for as long as necessary, depending on the results of the follow-up examinations (OCT). The common recommendation is to take it in cycles of 90 days, with 60 days of treatment interrupted by a 30 day therapeutic window.

Unexpectedly, in the composition as described above, a synergistic effect occurs between *Desmodium* and chromium Ill salt, i.e., a greater effect of the combination of *Desmodium* and chromium Ill is observed compared to the additive effects that may be observed when taking identical compositions, each comprising only *Desmodium* or only chromium salt. Following a treatment according to the invention, a significant improvement in visual acuity was observed. Optical coherence tomography (OCT) examinations showed a reduction in the number of serous drusen (greater than 125 μm in height), an index conditioning the visual prognosis in AMD.

BRIEF DESCRIPTION OF THE DRAWINGS

This invention will be better understood, and details relevant thereto will become apparent, in the light of the description to be made of various alternative embodiments, in relation to the attached figures, in which.

EXAMPLE 1: LIST OF INGREDIENTS

Figure 1B:
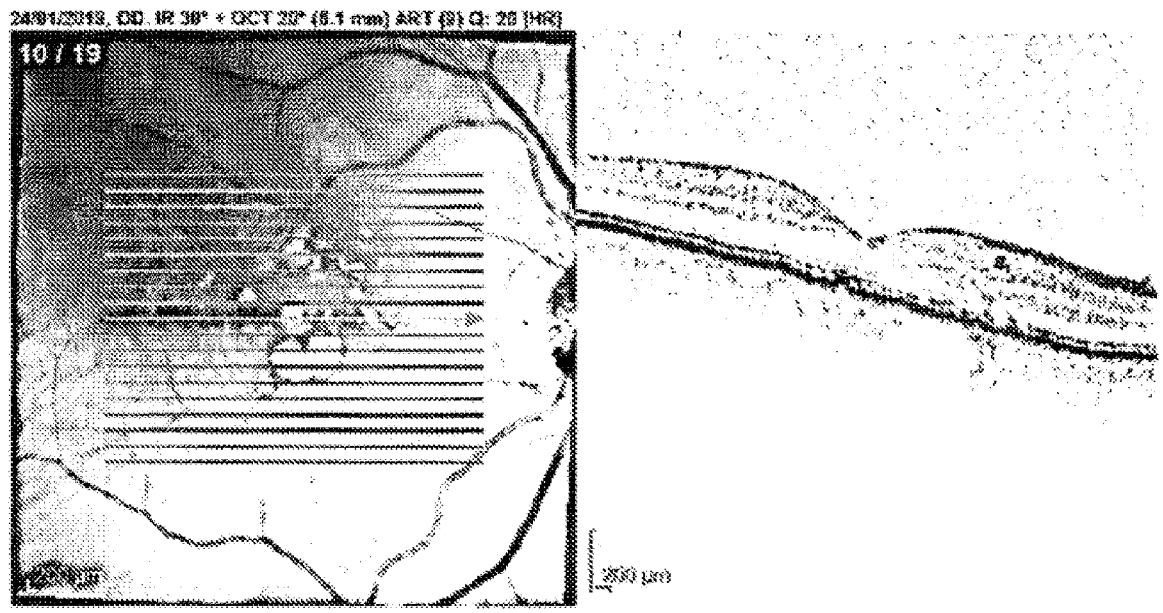
FIGS. 1*a* and 1*b* are images obtained by OCT of the right eye of a patient, before and after treatment with a composition according to the invention.

The ingredients below may be used to prepare a composition according to the invention in the following proportions. The quantities indicated correspond to daily doses. We note that some dosages are particularly high, which is suitable for AMD (according to the AREDS study).
*Desmodium adscendens*: between 400 to 800 mg
Chromium salt: chromium chloride between 0.10 mg and 0.25 mg, or
　chromium nicotinate between 0.10 mg to 0.25 mg, or
　chromium picolinate between 0.10 mg and 0.25 mg
Lutein: between 5 mg and 10 mg
Zeaxanthin: between 1 mg and 2 mg
Zinc: between 7 mg and 80 mg
Copper: between 0.5 mg and 2 mg
Omega-3 in the form of fish oil or microalgae, or plants including
DHA: between 180 mg and 502 mg (docosahexaenoic acid)
DPA: 100 mg (docosapentaenoic acid)
EPA: 650 mg (eicosapentaenoic acid)
Vitamin C: between 120 mg and 500 mg
Vitamin E: between 30 mg and 40 mg
Vitamin B1: between 0.50 mg and 1.10 mg
Vitamin B2: between 0.70 mg and 1.40 mg
Vitamin B3: between 8 mg and 16 mg
Vitamin B4: between 400 mg and 500 mg
Vitamin B6: between 0.70 mg and 1.40 mg
Vitamin B8: between 0.025 mg and 0.035 mg
Vitamin B9: between 0.1 mg and 0.2 mg
Vitamin B9: between 0.1 mg and 0.2 mg
Vitamin B12: Between 0.00125 mg and 0.0025 mg

EXAMPLE 2: FORMULATIONS

The quantities indicated correspond to daily doses.
Formulation 1:
　*Desmodium adscendens* 600 mg, leaves
　Chromium Nicotinate 0.2 mg (mass of chromium supplied)

This solid composition may be administered in 1 or 5 capsule doses per day.
Formulation 2:
　*Desmodium adscendens* 600 mg, leaves and stems
　Chromium chloride 0.2 mg (mass of chromium supplied)

This composition may be presented in liquid form in ampoules or vials. It may also be presented in a two-unit package, one in a capsule containing *Desmodium adscendens* powder, the other in an ampoule containing chromium chloride solution. It may be administered in 1 or 2 daily doses.
Formulation 3:
　*Desmodium adscendens* 600 mg, leaves
　Chromium Picolinate 0.2 mg (mass of chromium supplied)

This solid composition may be administered in 1 or 5 capsule doses per day.
Formulation 4:

| | |
|---|---|
| Desmodium adscendens | 400 mg |
| Chromium Chloride | 0.1 mg (mass of chromium supplied) |
| Lutein | 5 mg |
| Zeaxanthin | 1 mg |
| Omega-3 | 300 mg including DHA 180 mg |
| Zinc | 7.5 mg |
| Vitamin C | 90 mg |
| Vitamin E | 15 mg |

This composition may be divided into 3 capsules and 1 ampoule administered in 1 to 2 doses distributed throughout the day.
Formulation 5:

| | |
|---|---|
| Desmodium adscendens | 600 mg |
| Chromium Nicotinate | 0.2 mg (mass of chromium supplied) |
| Lutein | 5 mg |
| Zeaxanthin | 1 mg |
| Omega-3 | 338 mg including DHA 251.5 mg, EPA 56.50 mg, DPA 37.50 mg |
| Zinc | 7.5 mg |
| Copper | 0.5 mg |
| Vitamin C | 90 mg |
| Vitamin E | 15 mg |
| Resveratrol | 0.50 mg |

This solid composition may be divided into 6 capsules administered in 1 or 2 doses spread over the day.
Formulation 6:

| | |
|---|---|
| Desmodium adscendens | 600 mg |
| Chromium Picolinate | 0.20 mg (mass of chromium supplied) |
| Lutein | 5 mg |
| Zeaxanthin | 1 mg |
| Omega-3 | 185 mg DHA |
| Vitamin C | 60 mg |
| Vitamin E | 15 mg |
| Vitamin B1 | 0.55 mg |
| Vitamin B2 | 0.7 mg |
| Vitamin B3 | 8 mg |
| Vitamin B6 | 0.7 mg |
| Vitamin B8 | 0.025 mg |
| Vitamin B9 | 0.1 mg |
| Vitamin B12 | 0.00125 mg |

This solid composition may be divided into 6 capsules administered in 2 or 3 doses spread over the day.

Formulation 7:

| | |
|---|---|
| *Desmodium adscendens* | 600 mg powder or drinkable equivalent |
| Chromium Chloride | 0.20 mg (mass of chromium supplied) |
| Lutein | 10 mg |
| Zeaxanthin | 2 mg |
| Zinc | 7.5 mg |
| Schizochytrium | 500 mg Omega-3 including DHA 32% ± 2 or 160-170 mg and DPA 4% ± 2 or 20-30 mg |
| *Aphanizomenon flos Aquae* | 20 mg |
| Vitamin C | 120 mg |
| Vitamin E | 30 mg |
| Vitamin B1 | 0.55 mg |
| Vitamin B2 | 1 mg |
| Vitamin B3 | 8 mg |
| Vitamin B4 | 400 mg |
| Vitamin B6 | 1 mg |
| Vitamin B8 | 0.025 mg |
| Vitamin B9 | 0.1 mg |
| Vitamin B12 | 0.0025 mg |

Formulation 8:

| | |
|---|---|
| *Desmodium adscendens* | 600 mg powder or drinkable equivalent |
| Chromium Nicotinate | 0.20 mg (mass of chromium supplied) |
| Lutein | 10 mg |
| Zeaxanthin | 2 mg |
| Zinc | 7.5 mg |
| Odontella | 500 mg Omega-3 including DHA 32% ± 2 or 160-170 mg and DPA 4% ± 2 or 20-30 mg |
| Spiruline | 20 mg |
| Vitamin C | 120 mg |
| Vitamin E | 30 mg |
| Vitamin B1 | 0.55 mg |
| Vitamin B2 | 1 mg |
| Vitamin B3 | 8 mg |
| Vitamin B4 | 400 mg |
| Vitamin B6 | 1 mg |
| Vitamin B8 | 0.025 mg |
| Vitamin B9 | 0.1 mg |
| Vitamin B12 | 0.0025 mg |

EXAMPLE 3: TESTS

Abbreviations used: —RE: Right eye —LE: Left eye —OCT: Optical Coherence Tomography Period No. 1

Initial state: Presence for several years of macular remodeling with alteration of the left epithelium and discrete clouding of the lens in the right eye.

Treatment: CA1 food supplement for ocular purposes of known type at a rate of 2 capsules/d.

| Content of 1 capsule of food supplement CA1 (trade name Preservision3 ®): | |
|---|---|
| omega-3 | 300 mg (including DHA 180 mg) |
| Lutein | 5 mg |
| Zeaxanthin | 1 mg |
| Vitamin C | 90 mg |
| Vitamin E | 15 mg |
| Zinc | 7.5 mg |

Effect/Result: Despite this treatment, a sharp drop in distance vision occurred. Visual acuity increased in a few months, from 0.8 to 0.6 (RE and LE).

Period No. 2

Initial state: Ophthalmologic consultation indicates that visual acuity has fallen to 0.6 (RE and LE). Fundus examination of the right eye shows pigmentary remodeling of the macula and suspected drusen in the left eye.

Treatment: Food supplement CA1 at a rate of 1 capsule/d and chromium chloride at a rate of 100 µg/d (drinkable aqueous solution).

Effect/Result: After 6 months, visual acuity is stable for both eyes RE LE 0.6. The examination shows a pigmentary remodeling of the macula. The diagnosis of ODG dry AMD is made, with the presence of several confluent drusen. However, after one year, visual acuity deteriorated sharply (0.3 LE and 0.6 RE). The OCT examination shows serous drusen (whose height is 125 µm) in significant numbers: 6 drusen in the right eye (measured heights 122, 125, 140, 176, 214, and 197) and 6 drusen in the left eye (measured heights 128, 131, 169, 125, 124 and 123). Nevertheless, there is no intraretinal exudation (no neovessels), indicating no progression to wet AMD with neovessels at this stage. The CA1 food supplement and the associated chromium salt did not improve the patient's condition.

Period No. 2

Initial state: Acuity RE 0.6; LE 0.3. Presence of numerous serous drusen, no intra-retinal exudation.

Treatment: The treatment is in accordance with Formulation 4 given in Example 1 above. It corresponds to the treatment of the previous period (CA1 1 capsule, and chromium chloride 100 µg per day) to which *Desmodium adscendens* 400 mg/d is added.

Effect/Result: Macular state stable, slight improvement is observed LE 0.25.

Period No. 4

Initial state: Acuity RE 0.6; LE 0.25. Presence of serous drusen, no intra-retinal exudation.

Treatment: The treatment is changed with the following daily doses: CA1 (1 capsule) and increased intake of 600 mg of *Desmodium adscendens* and 200 µg of chromium salt, for 2 months then 1 month off.

Effect/Result: At the end of six months, the OCT examination revealed a decrease in drusen, with the disappearance of serous drusen in the left eye, the right eye still bearing six druses. Visual acuity was measured at RE 6/10 and LE 4/10, showing marked improvement. The fundus of the eye shows micro-atrophy in both eyes. Thus, the combination of *Desmodium* and chromium III has a noticeable and rapid effect on visual acuity and reduces drusen.

Period No. 5

Initial state: Favorable evolution of the vision and regression of the drusen.

Treatment: In view of the improvement obtained previously, the treatment is maintained but without interruption for one month out of three.

Effect/Result: After 5 months of continuous treatment, the biological assessment discovers an increase in urinary chromium to 31.54 nmol/l. It is, therefore, preferable to reduce the intake of chromium over the long term. The treatment is modified by reintroducing one month off per quarter. After one trimester, tests indicate an incipient decrease in urinary chromium levels (≤2 nmol/l).

Period No. 6

Initial state: Visual acuity measured in improvement compared to the previous semester, at RE 6/10 and LE 4/10. Presence of chromium above normal in urine.

Treatment: The combination of *Desmodium adscendens* 600 mg and chromium chloride 200 µg is maintained and is included in Formulation 5, as given in Example 1 above, taken for 2 months and then stopped for 1 month.

Effect/Result: Within one year, visual acuity improved significantly with 9/10 RE and 9/10 LE, an improvement of 3/10 (RE) and 5/10 (LE). The OCT shows a clear decrease in serous drusen: 4 drusen persist in the right eye (measured heights 149, 137, 169 and 130), and no drusen greater than 125 µm in the left eye. Blood chromium monitoring indicates a return to normal 0.52 µg/L). Thus, the drusen did not progress. Formulation 5 helped stabilize the MLA and improved vision.

Period No. 7

Initial state: Good level of visual acuity (0.9 in each eye) and stable drusen.

Treatment: *Desmodium adscendens* 600 mg is combined with 200 µg of chromium in the form of picolinate. They are included in Formulation 6, as in Example 1 above. The composition is administered in cycles in which it is taken for 1 months and then stopped for 1 month.

Effect/Result: Visual acuity was maintained at RE 7/10 and LE 8/10. The OCT examination shows that the drusen have regressed further: one druse of 145 µm (RE) and one of 126 µm (LE). Blood chromium is at a normal level. A decrease in vision to 0.7 and 0.8 could result from clouding of the lens (cataract). Formulation 6 allows satisfactory results to be obtained with regard to drusen regression.

Period No. 8

Treatment: Complete discontinuation of all treatment was observed over a period of 6 months.

Effect/Result: Visual acuity remained stable over the period. On the other hand, a slight increase in serous drusen was noted, and more importantly, numerous small drusen formed in both eyes, suggesting a resumption of the natural evolution of the pathology due to the cessation of the treatment.

Period No. 9

Initial state: Visual acuity RE 8/10 and LE 7/10.

Treatment: The treatment based on Formulation 5 given in Example 1 is administered with a one month break per quarter.

Effect/Result: Visual acuity remains stable (RE 7/10 and LE 7/10). The OCT examination shows a decrease in drusen (one drusen of 140 µm LE and no drusen RE). Resumption of treatment was necessary for a further regression of drusen.

Figure 1A:
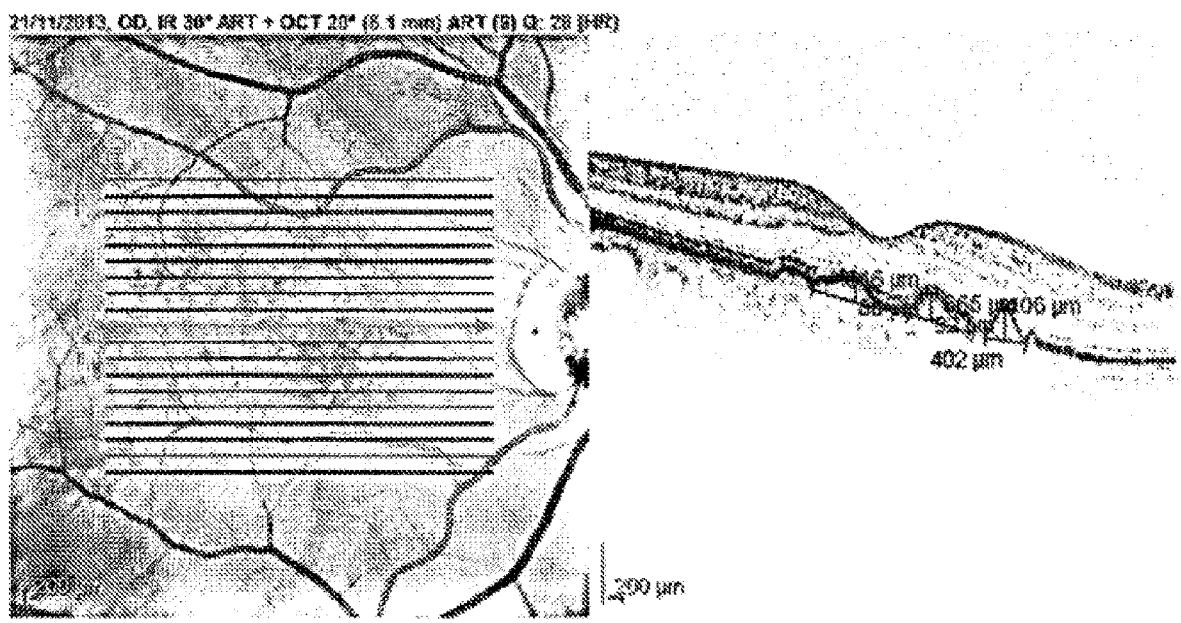
Figure 2B:
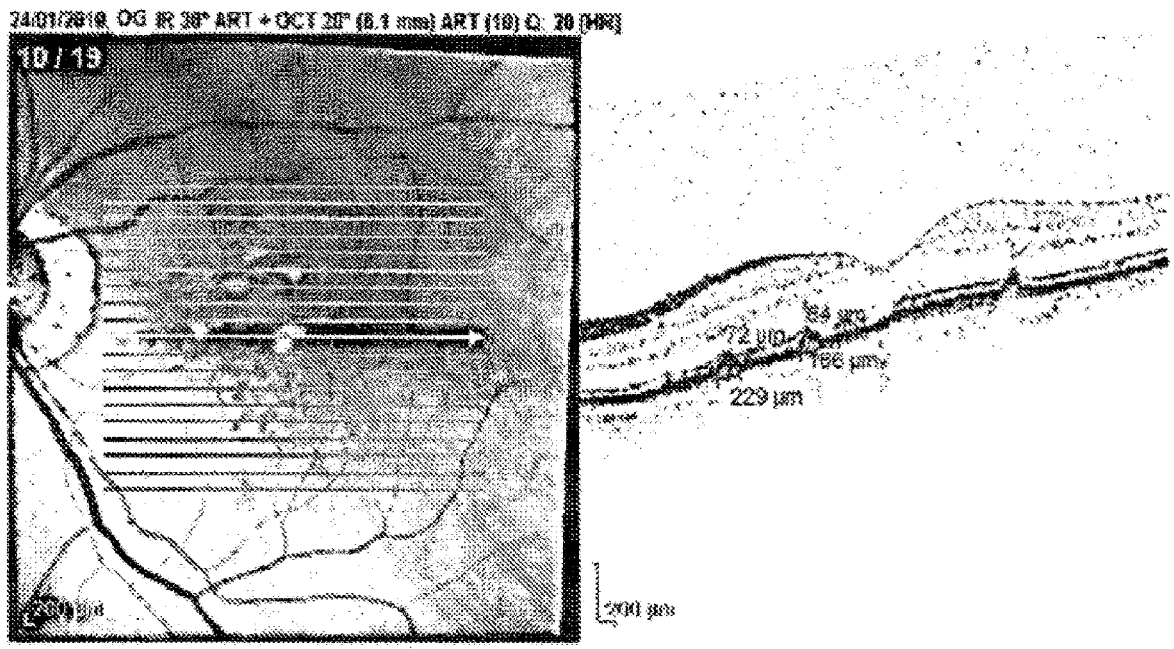
FIGS. 2*a* and 2*b* are OCT images of the left eye of the same patient, before and after treatment, with a composition according to the invention.
Figure 2A:
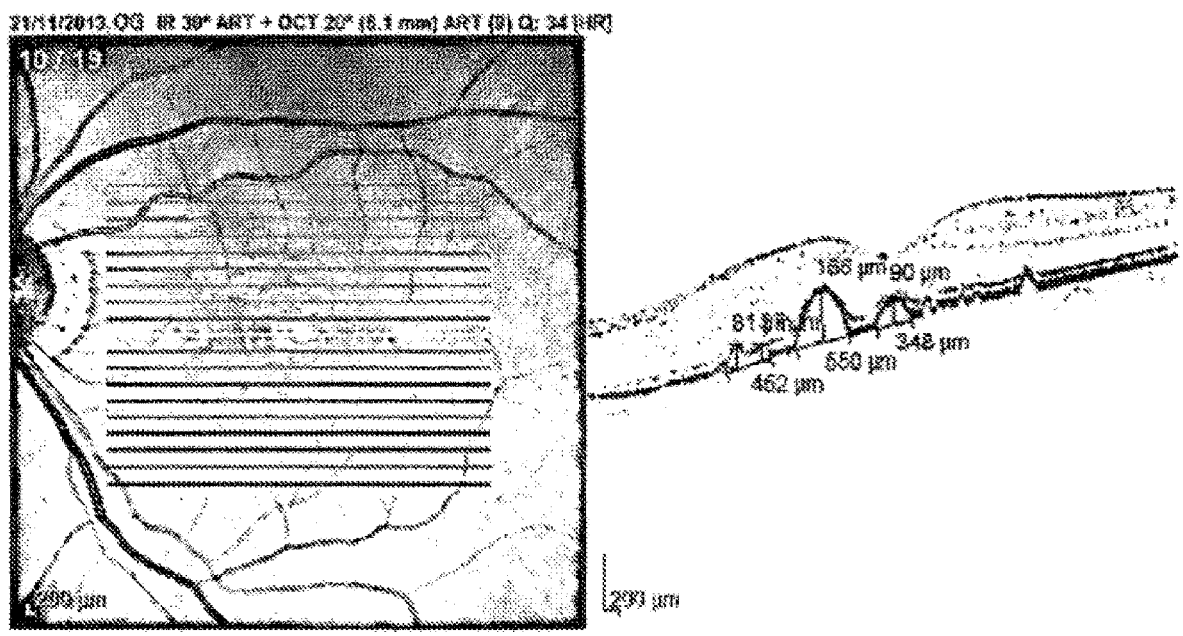

The improvement obtained is illustrated by the images of the OCT examinations given in FIGS. 1*a* and 1 *b* for the right eye and in FIGS. 2*a* and 2*b* for the left eye. They show the state of the macula following treatment with compositions in accordance with the invention (period No. 9, FIG. 1*b* RE and FIG. 2*b* LE) compared to that existing before treatment (FIG. 1*a* RE and FIG. 2*a* LE). The views are taken according to the same plan (at the level of the fovea) to allow comparison.

Formulation 5, administered in quarterly cycles of 2 months of treatment and 1 month of discontinuation, has been shown to be the most effective for the prevention and treatment of drusen in ARM and AMD, as well as for the preservation or improvement of visual acuity. This protocol respects biological balances, as shown by the analysis results.

What is claimed is:

1. A composition consisting of:
    a powder of *Desmodium adscendens* or *Desmodium gangeticum*; and
    a trivalent chromium salt.

2. The composition of claim 1, wherein the powder is obtained by grinding the leaves, stems, or aerial parts of a *Desmodium* plant.

3. The composition of claim 1, wherein the trivalent chromium salt is chromium chloride, chromium nicotinate, or chromium picolinate.

4. The composition of claim 1, wherein the composition comprises 0.2 mg to 1.2 mg of chromium III per gram of *Desmodium*.

5. The composition of claim 1, wherein the composition comprises 0.25 mg to 0.5 mg of chromium III per gram of *Desmodium*.

6. A method of preventing or treating a degenerative retinal pathology in a subject, wherein the method comprises:
    administering a composition according to claim 1 to the subject,
    wherein the degenerative retinal pathology is selected from the group consisting of age-related maculopathy, dry age-related macular degeneration, and wet age-related macular degeneration.

7. The method of claim 6, wherein the composition is administered daily in the form of one or two dose packs.

8. A composition consisting of:
    a powder of *Desmodium adscendens* or *Desmodium gangeticum* and
    a trivalent chromium salt;
    one or more vitamins; and optionally,
    one or more pigments;
    one or more omega-3 fatty acids; and/or
    one or more algae.

9. The composition of claim 8, the composition consisting of the powder of *Desmodium adscendens* or *Desmodium gangeticum*, the trivalent chromium salt; one or more vitamins; one or more pigments; one or more omega-3 fatty acids; and, optionally, one or more algae.

10. The composition of claim 8, wherein the composition is formulated for oral administration as a capsule, tablet, softgel, or liquid, and wherein the composition is formulated alone or with at least one excipient or additive.

11. The composition of claim 8, wherein the composition is formulated as a medication, phyto-medication, medical device, food supplement, or mixed with a food product.

12. The composition of claim 8, wherein the one or more vitamin is selected from the group consisting of vitamin C, vitamin E, vitamin B1, vitamin B2, vitamin B3, vitamin B4, vitamin B6, vitamin B8, vitamin B9, and vitamin B 12.

13. The composition of claim 8, including one or more pigment selected from the group consisting of lutein and zeaxanthin.

14. The composition of claim 8, including the omega-3 fatty acid, and wherein the omega-3 fatty acid is selected from the group consisting of a dry microalgae grind, an oil, or a fatty paste of *Schizochytrium*, a dry microalgae grind, an oil, or a fatty paste of *Odontella aurita*, a dry grind, an oil, or a fatty paste of flax seed, or a mixture thereof.

15. The composition of claim 9, wherein the composition consists of from 30% to 75% of *Desmodium* and trivalent chromium salt, from 10% to 30% of vitamin, from 0.5% to 2.5% of lutein and zeaxanthin, and from 25% to 60% of a *Schizochytrium* or *Odontella* oil, by mass relative to the total mass of the composition.

16. The composition of claim 8, wherein the composition consists of from 60% to 65% of *Desmodium* and trivalent chromium salt, from 15% to 18% of vitamins, from 0.75% to 1.5% of lutein and zeaxanthin, and from 30% to 40% of a *Schizochytrium* or *Odontella* oil, by mass with respect to the total mass of the composition.

17. The composition of claim 8, including one or more algae selected from a powder of *Aphanizomenon flos-aquae* or *Spirulina*.

18. The composition of claim 1, wherein the composition is formulated for oral administration as a capsule, tablet, softgel, or liquid, and wherein the composition is formulated alone or with at least one excipient or additive.

19. The composition of claim 1, wherein the composition is formulated as a medication, phyto-medication, medical device, food supplement, or mixed with a food product.

20. A method of preventing or treating a degenerative retinal pathology in a subject, wherein the method comprises:
   administering a composition according to claim 8 to the subject,
   wherein the degenerative retinal pathology is selected from the group consisting of age-related maculopathy, dry age-related macular degeneration, and wet age-related macular degeneration.

21. The method of claim 11, wherein the composition is administered daily in the form of one or two dose packs.

* * * * *